United States Patent [19]

Dixon, Jr. et al.

[11] 4,291,988
[45] Sep. 29, 1981

[54] AUTOMATED PATH DIFFERENCING SYSTEM

[75] Inventors: Richard G. Dixon, Jr., Las Cruces, N. Mex.; Wendell R. Watkins, El Paso, Tex.

[73] Assignee: The United States of America as represented by the Secretary of the Army, Washington, D.C.

[21] Appl. No.: 164,206

[22] Filed: Jun. 30, 1980

Related U.S. Application Data

[63] Continuation of Ser. No. 907,653, May 22, 1978, abandoned.

[51] Int. Cl.³ .............................................. G01N 21/01
[52] U.S. Cl. .................................... 356/437; 350/289; 350/294
[58] Field of Search ................................ 356/432–440, 356/442, 400; 350/289, 293, 294, 299, 300

[56] References Cited

U.S. PATENT DOCUMENTS

| | | | |
|---|---|---|---|
| 2,303,115 | 11/1942 | Eidmann et al. | 318/700 X |
| 2,729,143 | 1/1956 | White | 350/294 |
| 3,437,954 | 4/1969 | Herriott et al. | 350/294 X |
| 3,518,001 | 6/1970 | Hell | 356/300 |
| 4,100,471 | 7/1978 | Pritchard | 318/138 X |

OTHER PUBLICATIONS

White, J. V., "Long Optical Paths of Large Aperture", JOSA, vol. 32, p. 285, May 1942.
McCubbin, Jr. et al., "A White-type Multiple-Pass Absorption Cell of Simple Construction", Applied Optics, vol. 2, No. 7, Jul. 1963.
Edwards, T. H., "Multiple-Traverse Absorption Cell Design", vol. 51, No. 1, Jan. 1961.

*Primary Examiner*—John K. Corbin
*Assistant Examiner*—Bruce Y. Arnold
*Attorney, Agent, or Firm*—Nathan Edelberg; Jeremiah G. Murray; Edward Goldberg

[57] ABSTRACT

Nearly time independent measurements of low-absorption coefficients of atmospheric constituents can be made with long-path absorption cells by obtaining short-term averages of transmittance values related to cell mirror reflectivity through rapid changes in the cell pathlength between short and long multipaths.

7 Claims, 9 Drawing Figures

AUTOMATED PATH DIFFERENCING SYSTEM

The invention described herein may be manufactured and used by or for the Government for governmental purposes without the payment of any royalties thereon or therefor.

This is a continuation, of application Ser. No. 907,653, filed May 22, 1978, now abandoned.

FIELD OF THE INVENTION

This invention relates to the operation of long-path absorption cells, and, more particularly, to techniques to ease their alignment and to improve their accuracy of measurement of low absorption coefficients of atmospheric constituents.

BACKGROUND OF THE INVENTION

As will be appreciated by those skilled in the art, military applications of electro-optical systems require a knowledge of low-absorption coefficients of atmospheric constituents. This is so, for example, whether high energy lasers are utilized, or long-range laser and broadband systems, such as laser designators, range finders, image intensifiers, infrared images, and remote wind sensors, etc., are employed. Techniques for making these measurements have typically employed long-path absorption cells, but more recently, path differencing systems have been constructed which greatly reduce the data acquisition time and increase the measurement accuracy available. In essence, these advances effectively give to the massive cells and intricate optical and detection systems of the single-beam long-path absorption cell arrangements the real-time calibration of smaller double-beam spectrometer systems.

However, whereas the path differencing system of measurement represented a significant improvement over the long-path absorption cell arrangement, two persons were needed to perform the measurements—one, at the drive controls for the system, at one end of the cell, and the other, at the output of the system, the opposite end of the cell, some meters away. Additionally, some difficulty was experienced in rapidly and accurately repositioning and changing the beam pathlength, due, in part, to the limited torque capabilities of the available linear drives for the vacuum feedthrough pressure rods employed.

SUMMARY OF THE INVENTION

As will become clear hereinafter, the automated path differencing system of the present invention employs remote selsyn motors and a modified gear design to overcome these problems, and, at the same time, is effective to obtain short-term time averages of transmittance values related to cell mirror reflectivity by rapidly changing the cell pathlength between a short and long multipath. To accomplish the needed rapid, yet precise, repositioning of the cell output beam at both a long and a short multipath, the automated path differencing system will be seen to incorporate (1) a spring loading of the vacuum pressure drive rod which is used for cell mirror adjustments, (2) a non-rotating precision micrometer drive, (3) a low-torque reducing gear, (4) step up gears for rapid changes between multipaths, and (5) a remote operation of the mirror positioning controls used to obtain co-linear alignment between the light source of interest and a visible alignment source. Nearly time independent results, with the ability of a single individual to obtain state-of-the-art measurement accuracies with a long path absorption cell, have followed from the use of these modifications.

BRIEF DESCRIPTION OF THE DRAWINGS

These and other features of the invention will be more clearly understood from a consideration of the following description, taken in connection with the accompanying drawings in which.

DETAILED DESCRIPTION OF THE DRAWINGS

Figure 1:
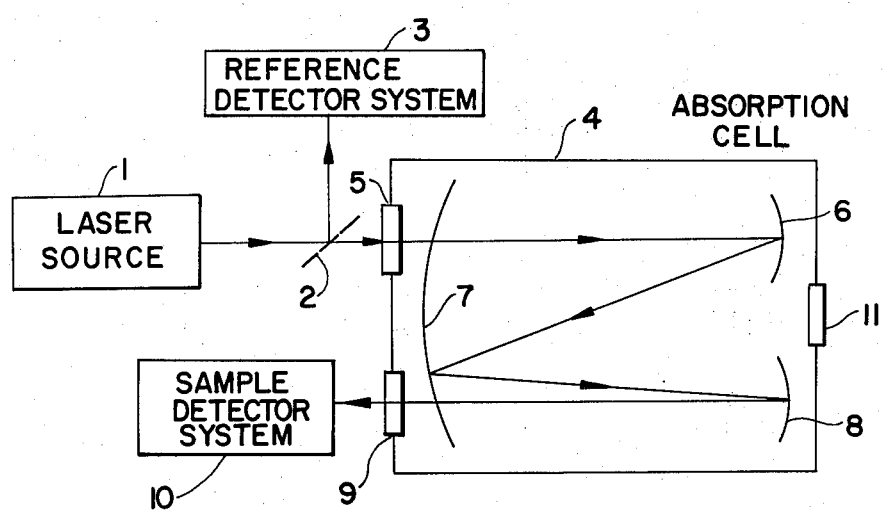
FIGS. 1–3 are helpful in an understanding of the technique of employing path differencing to obtain data from long-path absorption cells with reduced long-term drift error, and illustrate the problems encountered with such arrangements.
Figure 2:
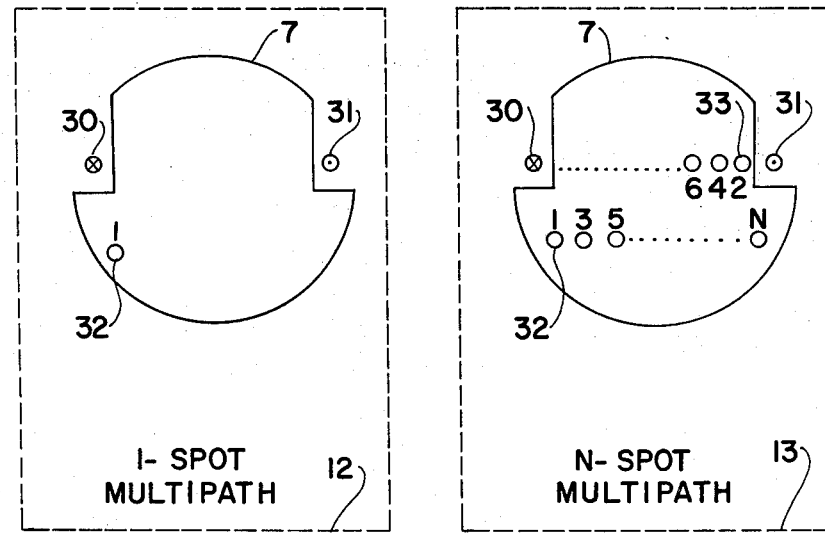

Referring now to the drawings, FIG. 1 illustrates a basic setup for a long-path absorption cell experiment using conventional White-type optics. A source of radiation 1, such as a laser, has its output divided into two portions by a beam splitter 2. One portion of the output is coupled to a reference detector system 3, while the other portion of the output beam enters the absorption cell 4 through a window 5. Multiple reflections are produced by spherically concave mirrors 6, 7, and 8, before the beam exits the cell through another window 9, from whence it is coupled to a sample detector system 10. The pathlength in the cell 4 can be determined by counting the number of reflection spot images in the multipath on mirror 7, as seen through an observation window 11. A short multipath of 1-spot 12 and a long multipath of N-spot 13 are shown in FIG. 2, and are obtained by adjusting only mirror 8, once the mirrors 6 and 7 are appropriately positioned, as described hereinafter.

As will be understood, absorption coefficients of gases are measured by using a path differencing technique of rapidly taking reference and sample detector signal data for short 1-spot and long N-spot multipaths. That is, absolute cell transmittance values for the optical path difference between an N-spot and a 1-spot multipath are obtained by taking short-term averaged ratios of relative transmittances (sample divided by reference detector signals) for the N-spot and 1-spot multipaths. The cell transmittance values obtained contain mirror reflectance loss and gaseous absorption contributions, and two such cell transmittance values are needed to obtain the absorption coefficient for a specific gas—one for a cell atmosphere with the absorbing gas and one for a cell atmosphere without the absorbing gas. In order to obtain good accuracy in low absorption coefficient measurements, the long-term drift error which plagues long-path absorption cells must be substantially reduced, and is done so by path differencing, with its rapid changes in cell pathlength, including precision beam positioning. As exact repositioning of the beams formed on mirror surfaces is essential in reducing long-term system drift, the long-path absorption cell optical systems which are designated to maximize output beam stability by use of compensating optics cannot be used because they do so at the expense of mirror reflection loss reproducibility. This is because the systematic cancellation of beam wander by the optical system inherently precludes the checking of exact beam positioning on the mirror surfaces.

Figure 3A:
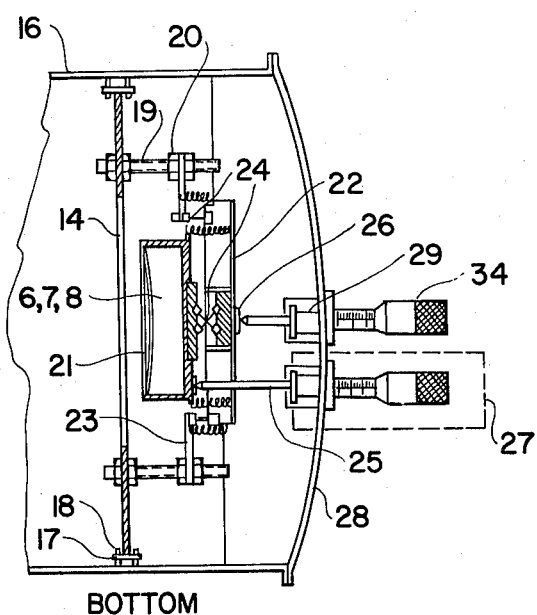
Figure 3B:
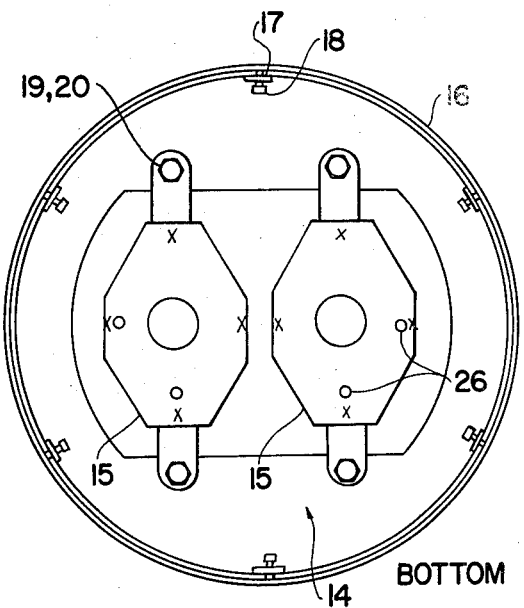

The side and end views of FIGS. 3A and 3B show the basic components of a representative 21 meter long-path absorption cell system, and illustrates a manner of mounting the spherically concave mirrors 6, 7, 8. Mounting rings 14 (one in each end of the cell 4) support the cell mirror holders 15 and mirrors 6-8, and are secured to the cell wall 16 by a set of pressure plates 17 and bolts 18. Each mirror holder 15 is attached to the mounting ring 14 on two large threaded bolts 19, and secured by pairs of nuts 20. Positioning of the mirror holders 15 along the length of the cell 4 is thus made possible.

The mirror holders 15 consist of three parts which are connected together—the first 21 to the second 22, and the second 22 to the third 23—by two sets of spring loaded flexures 24. These flexures 24 allow rotation of the mirror-holding portion 21 of the mirror holder 15 about the vertical and horizontal axes of the mounting ring 14, by moving two pressure rods 25 in or out along the length of the cell 4. These pressure rods 25 push against contact plates 26, are on linear motion feed-throughs 27, and are attached to a double-mirror-end flange 28 of the cell 4 by a flanged vacuum bellows 29. This allows the mirror holders 15 to be adjusted from outside the evacuable cell 4. The single-mirror-end pressure rods 25 are threaded into the mounting portion of the mirror holder and are initially positioned inside the cell 4. Additional adjustment of the single mirror 7 is not needed.

In typical operation, the spherically concave mirror 7 is at one end of the absorption cell 4 and the spherically concave mirrors 6 and 8 are at the other end. The radii of curvature of the three mirrors 6, 7, and 8, and the separation between the mirror 7 and either of the mirrors 6 and 8 are all of equal length, L, to form a beam conserving system. The f-number of the entrance beam into the cell 4 is adjusted, by a pair of concave mirrors (not shown) placed between the laser source 1 and the beam splitter 2 of FIG. 1, to focus the beam in the plane of the mirror 7 and to irradiate a large portion of the mirror 6. Mirror 6 focuses the beam onto the mirror 7, and the beam diverges to fill a large portion of the mirror 8 and then passes out of the absorption cell 4.

However, the above optical configuration does not not give the best beam conservation. Focusing on the surface of mirror 7 can greatly accentuate the effects of mirror imperfections, such as a speck of dust or a small pit, in terms of mirror reflection losses and reproducibility. To avoid such degradation, a collimated beam a few millimeters in diameter is introduced into the cell, which the mirror 6 focuses midway along the length of the cell; mirror 7, likewise, directs a collimated beam to mirror 8, which in turn focuses it, also midway along the length of the cell. The cell output beam (indicated by the reference numeral 30 in FIG. 2) thus is a diverging beam of the same diameter as the input beam to the cell (indicated by reference numeral 31 of FIG. 2). Such configuration limits the maximum obtainable pathlength of the cell 4 because the spots on mirror 7 are not focused to a small diameter; but as no beams are focused on any mirror surface, a far better beam conservation results.

In setting up the apparatus of FIGS. 1–3, the input beam 31 has its f-number adjusted so that it is focused inside the absorption cell 4 just off the input window upper right edge of mirror 7 and in the plane of its reflecting surface, as shown at 31 in FIG. 2. The diverging beam from this focal point is then centered on the surface of mirror 6, which is adjusted to focus the reflected beam directly below the output window upper left edge of mirror 7, as shown at 32 in FIG. 2. If the beam does not focus on the surface of mirror 7, then the separation distance between mirrors 6 and 7 is not equal to their radii of curvature, and mirror 6 is repositioned and the above procedure repeated until the beam from mirror 6 focuses at the surface of mirror 7. The diverging beam from the surface of mirror 7 is then centered on the surface of mirror 8 by adjusting mirror 7 about its horizontal and vertical axes. If the return beam does not also focus at the surface of mirror 7, then mirror 8 is moved closer to or further from mirror 7 until such focusing appears. Such adjustment maximizes the obtainable pathlength and minimizes the possibility of beam clipping inside the absorption cell 4. This is so, whether the input beam is focused in the plane of mirror 7, or whether a collimated input beam is used.

After the initial positioning of the cell mirrors 6, 7, and 8 has been performed, the absorption cell 4 can be sealed and used for measurements. To obtain maximum pathlength, the collimated input beam is positioned as close as possible to the upper right edge of mirror 7 without causing clipping, and is also centered in the middle of mirror 6. The adjustment of mirror 6 is critical for obtaining maximum pathlength, and for allowing rapid changes of the pathlength from 1-spot to N-spot multipaths with only mirror 8. The 1-spot 32 in FIG. 2 is positioned so that it is centered directly below the left edge of mirror 7 and an equal distance below the horizontal optical axis of mirror 7 as the output beam 30 is above the axis. This latter adjustment is performed in conjunction with vertical adjustment of the mirror 8. The 1-spot multipath output beam 30 can also be centered on the sample detector system 10 by adjusting mirror 8. If horizontal adjustment of the mirror 8 does not produce a long N-spot multipath output beam 30 which is centered vertically on the sample detector system 10, then the spot 32 on mirror 7 is appropriately raised or lowered by adjusting mirror 6, with corresponding vertical adjustment of mirror 8 until both the 1-spot and the N-spot outputs 30 are centered on the sample detector system 10.

In practice, the multipath outputs must be repositioned horizontally and vertically to within 1 millimeter (mm) for a 1-spot to 37-spot path difference. This path difference represents a pathlength of 1,512 meters (m) for the representative absorption cell 4 [i.e., $2(N-1)L$, where L=21 m], and puts restrictions on how precise the smallest adjustment of the linear feedthrough pressure rods 25 must be. In one construction, the contact points of the pressure rods 25 and mirror holders 15 are 114 mm from the corresponding axis of rotation, and a small angular rotation of mirror 8 will cause a corresponding angular offset of the output beam 30 of twice the rotation angle for each reflection from mirror 8, or 2 [(No. of spots+1)/2]=No. of spots+1. Hence, to obtain 1 mm repositioning error for a 37-spot output requires a linear motion error (x) of the pressure rods 25 of $$38(x)/(114 \text{ mm}) = (1 \text{ mm})/(21,000 \text{ mm})$$

or x=0.000143 mm or 0.143 μm. In addition, to be able to rapidly change pathlengths between 1-spot and N-spot multipaths requires the movement of the output beam for the 1-spot multipath (makes only one reflection from mirror 8) a distance of 279 mm in the plane of mirror 7 to the spot position 33 in a 37-spot multipath (FIG. 2). The corresponding linear motion (y) of the pressure rod controlling the vertical axis rotation is then $$2(y)/(114 \text{ mm}) = (279 \text{ mm})/(21{,}000 \text{ mm})$$

or y=0.757 mm.

In this arrangement, the pressure rods 25 were adjusted by using bakeable linear motion feedthroughs 27 manufactured by Ultek (Perkins Elmer) as Model No. 282-6200, having a 1.57 thread/mm micrometer spindle drive and an accuracy of 0.127 mm including backlash. To meet the requirement of rapidly changing pathlength required only a little over one revolution of the spindle, 34 in FIG. 3A, and was easily satisfied. Meeting the requirement of rapidly obtaining the repositioning of the output for a 37-spot multipath, on the other hand, was nearly impossible because the magnitude of the repositioning error of the micrometer was about one thousand times that required to meet the x repositioning demands. Two major problems were found to be inherent in such a system, excluding the minor problem of gear backlash. First, the torque required to obtain the drive accuracy needed was too small for direct, manual micrometer operation; and second, the drive controls for the system were at one end of the 21 m cell, whereas the cell output had to be viewed from the opposite end—i.e., 2 persons were needed to perform the measurements.

Figure 4A:
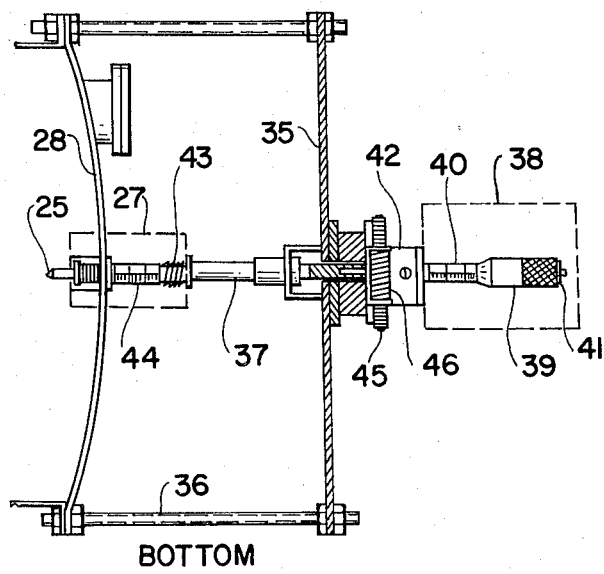
FIGS. 4 and 5 show various features of the automated path differencing system constructed according to the invention.
Figure 4B:
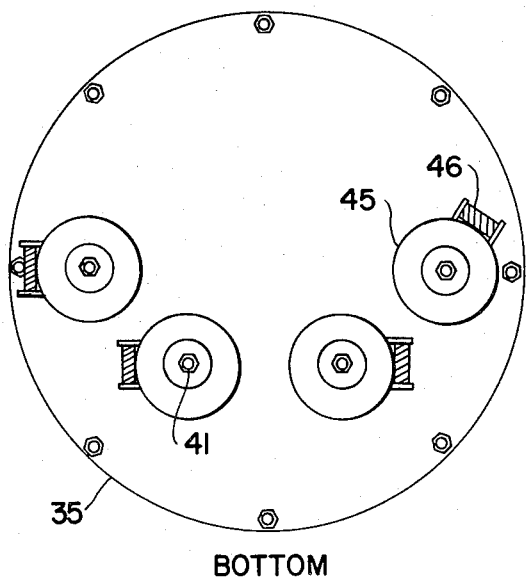

In accordance with the present invention, however, both these problems associated with the rapid repositioning can be eliminated through the use of a new drive gear design and remote selsyn (or synchronous) motors; and yet, the ability to rapidly change pathlengths between 1-spot and 37-spot multipaths can be retained. As far as the problem of spindle torque is concerned, several system components were added to the end of the cell to allow control of the pressure rods 25 from outside a 20 centimeter (cm) thick heating shell which is placed around the entire cell for bakeout and temperature control purposes. As shown in the side and end views of FIGS. 4A and 4B, a 1¼ cm thick aluminum base plate 35 was offset from the cell's double-mirror-end flange 28 by several 2½ cm diameter bolts 36. This plate 35 was used to rigidly hold all gears required to make fine adjustments of the four pressure rods 25. The linear motion feedthroughs 27 were used, but without the spindle 34, as used in FIG. 3A, attached, an extension rod 37 being threaded into the end of the pressure rod 25 instead. A Starrett micrometer 38 (Model 262RL, with 1.57 thread/mm drive) was attached to the end of the extension rod 37 and mounted to the outside of the aluminum plate 35. In addition, the operation of the micrometer 38 was altered: (1) the spindle 39 was secured to the drive rod 40 by tightening the end nut 41 after the rachet was removed; and (2) the allen bolt which screwed into the guide slot in the drive rod 40 was removed, to allow the drive rod 40 to rotate freely in the mounting sleeve 42 when the spindle-drive rod unit (which includes the spindle 39 attached to the drive rod 40) was threaded onto it. The result was a micrometer drive which, when the mounting sleeve 42 was rotated, a non-rotating drive of the spindle-drive rod 40 was obtained with only micrometer drive thread slop.

Even this problem was able to be eliminated, furthermore, by spring loading, as at 43, the pressure rod extension 37 against the linear motion feedthrough sleeve 44.

The problem of the small torque required to fine position the micrometer drive was alleviated by a precision, worm gear operated 25:1 reduction gear 45 mounted directly to the aluminum plate 35 and secured to the micrometer sleeve 42. Again, no rotation slop of the reduction gear 45 was encountered, because the whole drive mechanism was spring loaded (at 43) against the linear motion feedthrough sleeve 44, although there was a little slop in the worm gear 46—, but no corresponding linear motion of the pressure rod 25 resulted. With this new drive gear design, a 1-degree rotation of the worm gear 46 resulted in a pressure rod drive of 0.0706 μm, which was quite adequate for the precision repositioning of the long-path output beam.

Figure 5:
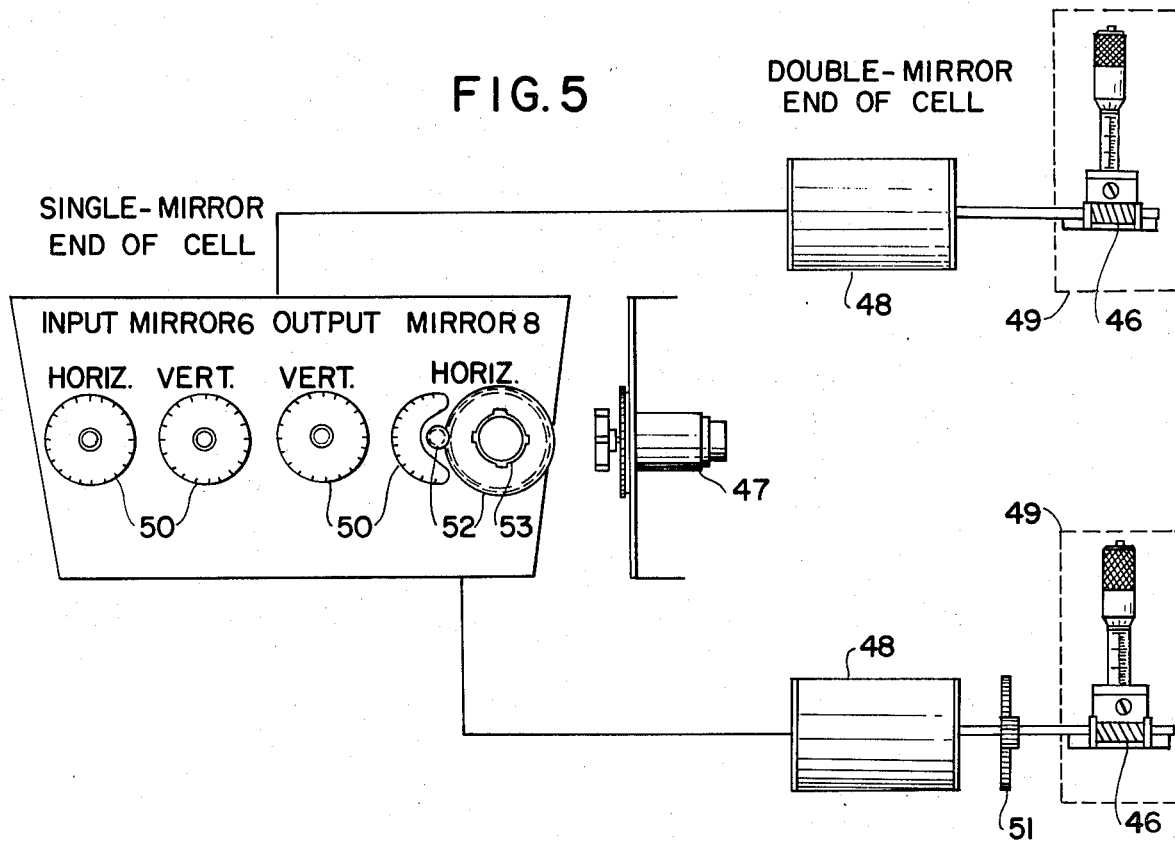

As far as the problem of remote control is concerned, a selsyn transmitter 47 and receiver 48 (FIG. 5) were used to obtain 1:1 remote drive of the worm gear 46 on the low-torque micrometer drive system 49. The selsyn transmitters 47 were controlled by a 7-cm diameter dial 50 graduated in degrees, and were located at the single mirror end of the absorption cell 4, where adjustment and observation of the cell output beam 30 (FIG. 2) could be done simultaneously. The procedure for aligning and changing cell pathlengths will be subsequently discussed, but, at this point, it would be helpful to discuss the mechanical requirements for rapid remote changes between long and short multipaths. For changing from a 1-spot to a 37-spot multipath in the 21-m cell, the pressure rod 25 must be driven 0.757 mm or 29.8 revolutions of the worm gear controlling the rotation of mirror 8 about its vertical axis. As this was impractical for rapid pathlength changes, two step up gears 51 and 52 were used to alleviate this system problem. First, a 1:4.75 step up gear 51 was used between the worm gear 46 and the selsyn receiver 48, to reduce the fine adjustment of the remote control of the linear pressure rod drive to 0.318 μm per degree rotation of the selsyn transmitter dial 50. (Obtaining the required 0.143 μm linear drive precision was still routinely possible.) Next, a coarse adjustment dial 53 was attached to the selsyn transmitter fine adjustment dial 50 by a 1:5 step up gear 52. As a result, only a little over one revolution of the coarse adjustment dial 53 was required to make the 1-spot and 37-spot multipath change, since the total gear step-up over the worm gear drive was 1:23.75. By using this arrangement, both remote beam positioning and rapid pathlength change requirements were satisfied.

As is well known and understood, the alignment of any optical system containing light sources is greatly facilitated when the sources are of visible wavelengths. This is especially true for the precision alignment required to perform long-path absorption cell experiments. A cw helium-neon (He-Ne) laser is usually used to obtain the optical system alignment required. The light source of interest, which in the case of most electro-optical and high-energy laser systems is in the infrared and hence is invisible to the naked eye, is then made to propagate colinear with the He-Ne laser.

Figure 6:
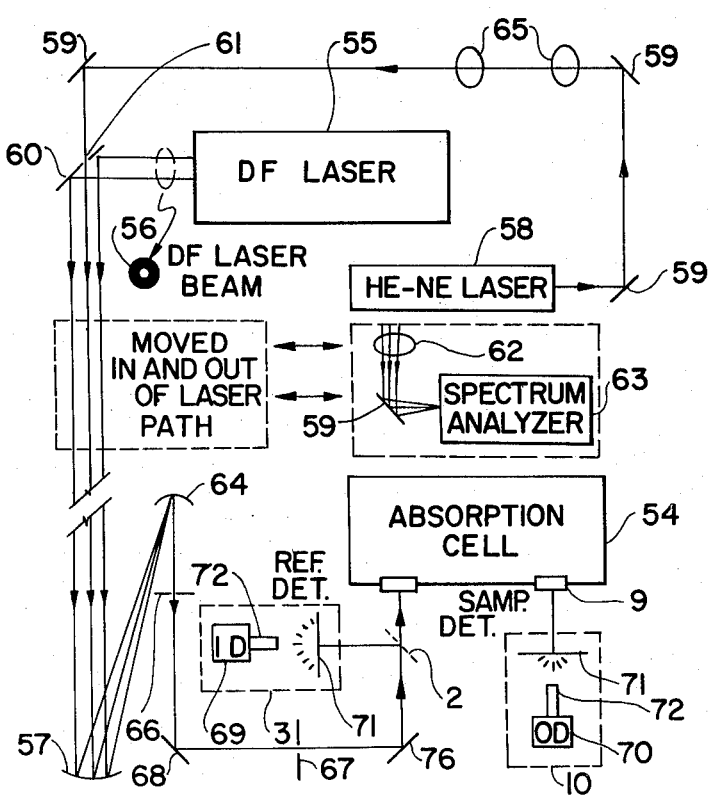
FIGS. 6 and 7 illustrate the remote operation of the mirror positioning controls in making long-path absorption cell measurements.

A detailed setup of an experiment using 21-m stainless steel White cell 54 and a line tunable pulsed deuterium fluoride (DF) laser source 55 (FIG. 6) illustrates the types of problems which are encountered in making long-path absorption cell measurements. A Lumonics Model TEA-201 pulsed (0.3 Hz), line tunable, DF laser 55 is used which has an unstable resonator front reflector and a grating back reflector for line selection. The resulting output 56 is donut-shaped in the near field and has a central maximum diffraction ring pattern in the far field (25 m away) where the beam is collected by a spherically concave mirror 57. The He-Ne alignment laser 58 is made colinear with the DF laser 55 by use of several flat mirrors 59, and one mirror 60 with a 1-cm diameter hole drilled through the center to allow the He-Ne beam to pass through. The donut-shaped DF beam, with an outside diameter of 4-cm and an inside diameter of 2-cm, is centered on mirror 60 about the central hole 61 by using a sheet of high sensitivity Edmund Scientific Company liquid crystal. The mode quality of the DF laser 55 was checked by focusing the 4-cm diameter near-field beam with a calcium fluoride lens 62 to a few millimeters in diameter and observing the focused beam on the liquid crystal. The laser front reflector and grating were adjusted to yield a donut-shaped pattern of uniform heating, while the wavelength of the DF laser 55 was checked by inserting a spectrum analyzer 63 into the beam, as depicted in the dashed box.

A 5-mm diameter collimated DF laser beam was obtained by collecting the central maximum and first ring of the far-field DF diffraction pattern with a 4-cm diameter aperture at mirror 57. Mirrors 57 and 64 were both spherically concave with focal lengths of 160 and 20 cm respectively, and were positioned on a 2-m optical bench approximately 180-cm apart and only slightly off-axis to the DF beam to minimize aberration. By appropriate adjustment of the separation between mirrors 57 and 64, a 5-mm diameter collimated DF laser beam was obtained. The beam quality was checked by propagating the DF beam the length of the 21-m cell 54 outside the cell, and observing its size with the sheet of liquid crystal.

The divergence of the DF and the He-Ne alignment laser was matched by inserting a beam telescope, having two lenses 65, in the He-Ne beam before the two beams were combined. By adjustment of the beam telescope focus, the He-Ne beam was made as nearly collimated as possible for the separation between mirrors 57 and 64 which gives a collimated DF beam. Several rings of an He-Ne diffraction pattern were collected by mirror 57 in this configuration. Two 1-cm diameter apertures 66 and 67 were placed in the beam after reflections from mirror 64, and from the first mirror 68 in the collection optics. The He-Ne diffraction pattern was centered on each of these apertures 66 and 67 to ensure uniform repositioning of the cell input beam 31 (FIG. 2) on a routine basis. The beam splitter 2 used was a 2-mm thick calcium fluoride flat which causes minimal separation of the He-Ne and DF laser optical axes due to wavelength dependent difference in their refraction by the optical flat. (It was found best to use a flat with one antireflection coated side to obtain only one reflected [in this case a DF laser] beam which goes to the input detector 69 of the reference detector system 3 and also to reduce etalon interference effects. If an optical wedge were used as the beam splitter, then a matched pair should be inserted into the beam at 45° to the beam, and orthogonal to each other, to essentially cancel the wavelength dependent refraction effects.) Care must be taken in selection of an appropriate beam splitter so as not to alter the colinearity of the He-Ne and DF lasers because of the exacting requirements of long-path absorption cell optical alignment.

Figure 7:
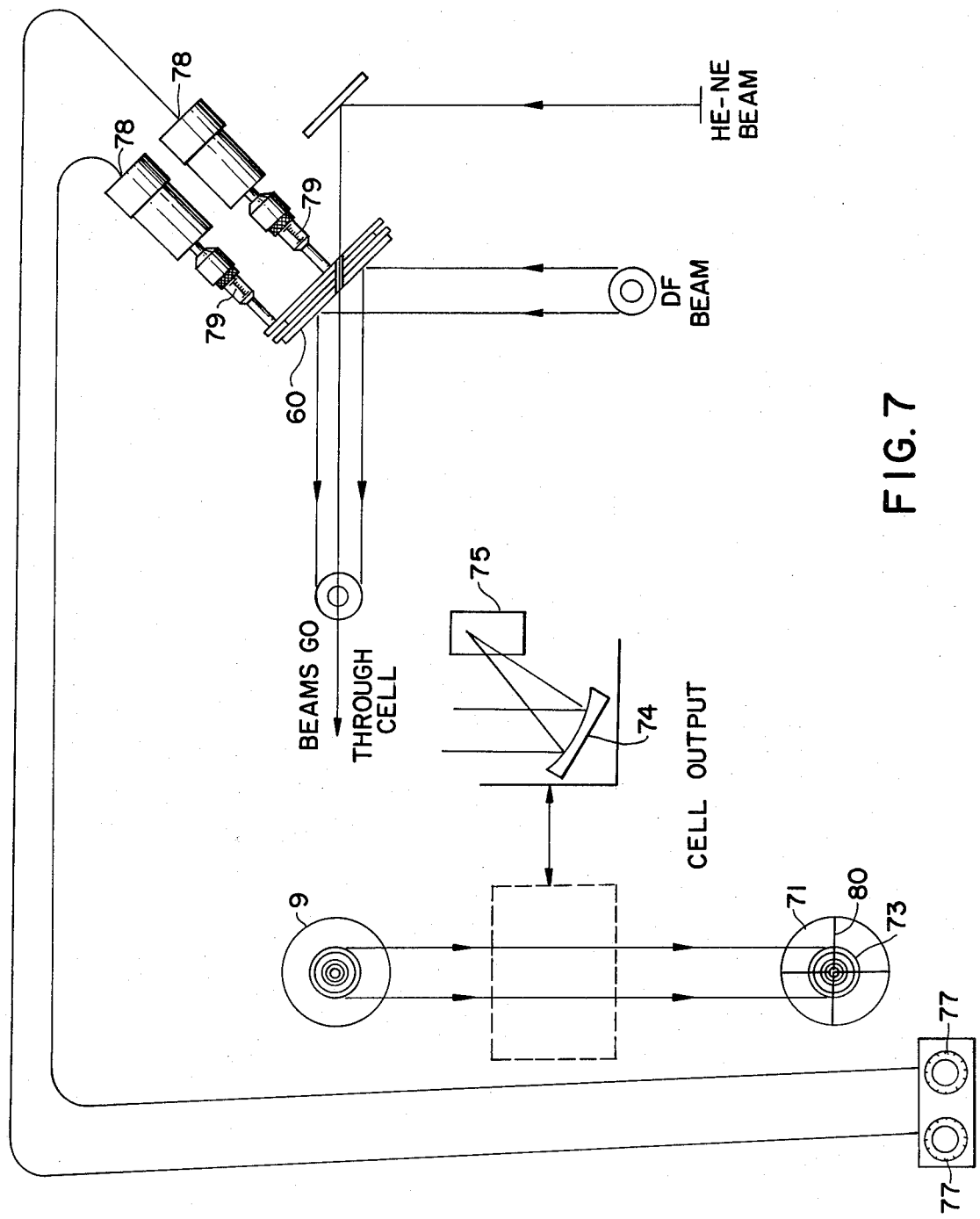

The two beams which go to the input detector 69 and output detector 70 of the reference and sample detector systems 3 and 10, respectively, were centered on cross hairs on specially selected diffuse transmittance filters 71 (diffuse reflectors could also be used). For the case of DF, Millipore LSWPO4700 Teflon membrane filters have relatively flat forward lobe diffuse transmittance, and work well as diffusers of DF radiation reducing the effects of beam jitter and wander. Apertures 72 were used to select a small enough solid angle of the diffused laser beam to ensure linear detector response. Additionally, the He-Ne alignment beam diffraction pattern 73 (FIG. 7) could be seen through the filter 71, which made repositioning easier. The colinearity alignment was performed on the output beams which pass through the cell output window 9 before they reached the sample diffusing filter 71. A short focal length spherically concave mirror 74 (also, FIG. 7) was inserted into the beams, which were focused onto an activated charcoal block 75 (as are typically used in spectrum analyzers). The focused pulsed DF laser beam caused a bright burn pattern on the charcoal block 75 which was centered on the focused He-Ne diffraction pattern 73 (slight adjustments of the cell input mirror 76 may be needed to ensure a uniform intensity He-Ne diffraction ring pattern 73 at long cell pathlengths). This adjustment was performed for each change to the long N-spot multipath 13 and, once performed, ensured colinearity for all shorter multipaths. The pathlength was determined by counting the number of image spots which crossed the output cell window 9 by observing the He-Ne laser beam on the membrane filter 71 between the 1-spot and N-spot multipaths. Again, a pair of selsyn transmitters 77 and receivers 78 were used to perform remote adjustments of the micrometers 79 of mirror 60 from the single mirror end of the absorption cell.

As far as the initial positioning of the multipath spot 32 (FIG. 2) is concerned, this spot is centered below the upper left edge of mirror 7, and its semicircle output beam vertically centered on the horizontal membrane filter crosshair 80 by adjusting mirror 6. The distance which the spot 32 must be lowered by mirror 6 to allow pathlengths to be changed from a 1-spot to an N-spot multipath using only vertical axis rotation of mirror 8 is determined as was previously discussed. Each time a series of data is taken, the spot 32 is lowered the same distance to ensure exact repositioning of the spot 32 on mirror 7.

It should be apparent that for military applications, these elaborate alignment procedures and techniques—to decrease the time required to change cell pathlengths—are necessary to obtain very accurate absorption coefficient measurements. Of paramount importance to the success of the path differencing arrangement is the obtaining of a short-term time average of the cell mirror reflectance loss for the path difference between a 1-spot and N-spot multipath. Data were taken with the arrangement of the invention over a 2-month time interval on 26 DF laser lines ranging from $P_{1-0}(2)$ at 3.5 $\mu$m to $P_{3-2}(11)$ at 4.0 $\mu$m for a reference gas filled cell of 760 torr of an 80/20 mixture of $N_2/O_2$ (which is essentially nonabsorbing except near 4.0 $\mu$m). The transmittance values for a 1.512 km path difference between a 1-spot and 37-spot multipath ranged from 0.11 to 0.17. Three sets of short-term path differencing time averages were taken for all 26 DF laser lines separated by a few weeks. The short-term time averages exhibited typically less than 2% error for eight path difference values. The long-term drift error was typically around ½% for the three data sets, which indicates very little systematic error. If a large number of short-term time averages were taken for a single laser line, the long-term reflectance loss may contain less than ½% error. Even with the ½% transmittance measurement accuracy for a 1.512 km path difference, absorptions of a few percent per kilometer have already been made.

While there has been described what is considered to be a preferred embodiment of the present invention, it will be appreciated by those skilled in the art that modifications may be made without departing from the scope of the teachings herein which permit several improvements in long-path absorption cell measurement capabilities as enable one person to operate a 21-m White cell and obtain state-of-the-art measurement accuracy. Whereas the described features include low-torque linear drives for vacuum feedthrough pressure rods, remote operation for cell mirror adjustment, and laser alignment using selsyn transmitters and receivers—as well as a variety of detection and alignment techniques—, it will be apparent that not all these features need be incorporated at the same time in order for measurement improvements to result. For at least such reason, therefore, reference should be had to the annexed claims for a true understanding of the scope of the invention.

What is claimed is:

1. In a system for measuring absorption coefficients of atmospheric constituents, apparatus comprising:
    an absorption cell having first, second and third spherically concave mirrors positioned such that reflections from said first mirror are reflected at one point by said second mirror to be reflected thereon at another point by said third mirror, said first and third mirrors being positioned at the far end of said cell and said second mirror being positioned at the near end of said cell, said cell including first and second windows spaced along said near end;
    first means at said near end for supplying a cylindrical hollow center input beam of coherent optical energy through said first window towards said first mirror;
    second means providing a reference beam of coherent optical energy through said first window;
    adjustable means at said near end for adjustably aligning said reference beam to pass through said hollow center of said input beam, said adjustable means including an apertured mirror, said hollow center of said input beam being aligned with the aperture in said mirror and said reference beam passing through said aperture;
    means adjacent said near end first window for detecting the alignment of said reference beam through said hollow center of said input beam;
    a third window at said far end for observing reflection images on said second mirror;
    means at said far end for adjusting the positioning of said first and third mirrors, the positioning of said third mirror providing rapid changes in the path length in the absorption cell between short and long multipaths;
    output means adjacent said near end second window for detecting and measuring the reflected images from said third mirror passing through said second window; and
    means at said near end for remotely controlling the positioning of said first and third mirrors at said far end.

2. The apparatus of claim 1 wherein said first, second and third mirrors are selected such that beam reflections from said first and third mirrors substantially focus at the surface of said second mirror.

3. The apparatus of claim 1 wherein said means at said far end for adjusting the positioning includes resilient linear motion pressure means for rotating said first and third spherically concave mirrors about vertical and horizontal axes thereof, and also includes reduction gear means operative in conjunction therewith to provide fine positioning control of said first and third mirrors.

4. The apparatus of claim 3 wherein said means at said near end for remotely controlling the positioning includes a plurality of selsyn transmitters at said near end, and a plurality of selsyn receivers at said far end controlling said reduction gear means in fine positioning said first and third mirrors.

5. The apparatus of claim 4 wherein said means at said far end for adjusting the positioning further includes step-up gear means operative in conjunction with said selsyn transmitter and receiver means for rapidly rotating said third spherically concave mirror in changing between short and long multipaths in said absorption cell.

6. The apparatus of claim 5 wherein said step-up gear means includes a first step-up gear operative with said selsyn receiver means to reduce the fine adjustment of the remote positioning control of said linear motion pressure means, and also includes a second step-up gear operative with said selsyn transmitter means.

7. The apparatus of claim 4 wherein said plurality of selsyn transmitters and receivers include respective units for control of horizontal and vertical movement of said first and third mirrors.

* * * * *